United States Patent [19]

Rawlins

[11] Patent Number: 4,859,709

[45] Date of Patent: Aug. 22, 1989

[54] PHARMACEUTICAL COMPOSITION

[75] Inventor: David A. Rawlins, Tewin, England

[73] Assignee: Beecham Group plc, Middlesex, England

[21] Appl. No.: 115,589

[22] Filed: Oct. 26, 1987

Related U.S. Application Data

[63] Continuation-in-part of Ser. No. 736,337, May 21, 1985, Pat. No. 4,719,228.

[30] Foreign Application Priority Data

May 23, 1984 [GB] United Kingdom ............... 8413191

[51] Int. Cl.$^4$ .............. A61K 47/00; A61K 31/705; A61K 31/56; A61K 31/54
[52] U.S. Cl. ................................ 514/770; 514/26; 514/169; 514/221; 514/420; 514/613; 514/646; 514/579; 514/884; 514/885; 514/886; 514/926; 514/927
[58] Field of Search ............... 514/770, 26, 169, 221, 514/420, 613, 646, 579, 884, 885, 886, 926, 927

[56] References Cited

U.S. PATENT DOCUMENTS 4,254,099  3/1981  Asmussen .

Primary Examiner—John W. Rollins
Attorney, Agent, or Firm—Hopgood, Calimafde, Kalil, Blaustein & Judlowe

[57] ABSTRACT

A pharmaceutical composition comprising a freely flowable powder, the powder comprising a porous, high absorption silica or silicate having absorbed therein at least 10% by volume of a liquid, pharmaceutically active composition, based on the weight of powder plus liquid, provided that when the liquid pharmaceutically active composition is a corticoid solution the silica or silicate has a mean particle size of at least 10 μm in diameter.

7 Claims, No Drawings

PHARMACEUTICAL COMPOSITION

This application is a continuation-in-part of 06/736,337 filed 5/21/85 now U.S. Pat. No. 4,719,228, issued Jan. 12, 1988.

The present invention relates to a pharmaceutical composition, and in particular to a composition in which the active ingredient is incorporated into a freely-flowable powder.

Hitherto, certain synthetic silicas have been used to absorb liquid pesticides, such as malathion, diazinon and parathion, to form freely-flowable powder concentrates which have good storage stability. Such silicas have also been used in a similar way to absorb liquid animal feed additives, such as ethoxyquin, molasses and choline chloride.

In addition corticoid solutions have been dispersed on amorphous porous silicas of small particle size (J.Pharm.Sci. 1984, 73 401–403).

It has now been found that silicas can be used to absorb liquid pharmaceutical compositions to form freely-flowable powder concentrates which, when administered in unit dose formulations, can provide more rapid and complete drug release than conventional drug containing formulations. This is of particular value for drugs, such as digoxin or phenytoin, where bioavailability problems exist.

According to the present invention there is provided a pharmaceutical composition comprising a freely-flowable powder, the powder comprising a porous, high absorption silica or silicate having absorbed therein at least 10% by volume of a liquid, pharmaceutically active composition, based on the weight of powder plus liquid, provided that when the liquid pharmaceutically active composition is a corticoid solution, the silica or silicate has a mean particle size of at least 10 μm in diameter.

Examples of useful silicas are precipitated silicas or xerogels. Examples of useful silicates are aluminosilicates or calcium silicates.

The silicas or silicates preferably have a liquid absorption capacity of from 100 to 300 mls per 100 g. of silica or silicate, as determined by the ASTM D281 or DIN 53199 methods. Preferred silicas are those marketed by Degussa under the Sipernat and Wessalon trade marks.

The preferred percentage by volume of liquid is from 30% to 75%, more preferably 40% to 75% v/w.

The silicas or silicates suitably have a mean particle size of at least 10 μm in diameter. Preferably the particle size is within the range of 10 μm to 1 mm in diameter.

Suitably the composition is in unit dosage form. Examples of unit dose formulations of the present invention include capsule and tablet formulations, preferably a capsule formulation.

Preferably for capsule formulations, the silicas or silicates may have a mean particle size within the range of 20 μm to 1 mm in diameter. A particularly preferred mean particle size is within the range of 30 μm to 500 μm in diameter.

Preferably for tablet formulations, the silicas or silicates may have a mean particle size within the range of 10 μm to 500 μm. A particularly preferred mean particle size is within the range of 50 μm to 500 μm in diameter more particularly of 150 μm to 250 μm in diameter.

The liquid, pharmaceutically active composition preferably comprises a pharmaceutically active ingredient in a liquid diluent or carrier. The active ingredient may be dissolved or dispersed in the liquid diluent or carrier, which may be a water miscible or water immiscible medium.

Examples of liquid diluents or carriers include the following three classes:
 (a) Water miscible carriers
   Propylene Glycol
   Polyethylene Glycol
   Water
   Solketal
   Glycofurol
   Dimethylisosorbide
   Nonionic surface active agents
 (b) Oils and Organic carriers
   Fractionated Coconut Oil
   Sesame Oil
   Soya Bean Oil
   Liquid Paraffin
   Isopropylmyristate
   Triacetin
 (c) Semi-solid carriers
   High molecular weight polyethylene glycols
   White soft paraffin An example of a pharmaceutically active ingredient is an anti-hypertensive agent.

Further examples of pharmaceutically active ingredients include anti-inflammatory agents, tranquilisers, cardiotonic agents, antibacterial agents, antidepressants, corticosteroids, anti-ulcer agents, anti-allergy agents, anti-obesity agents, anti-hyperglycaemic agents, anti-emetic agents and gastric motility enhancing agents.

The above described compositions are particularly useful when the pharmaceutically active ingredients have poor aqueous solubility and bioavailability problems, such as diazepam and digoxin.

A preferred class of pharmaceutically active ingredients is the class of anti-hypertensive agents, in particular those described in European Published Patent Application No. 0076075 such as 6-cyano-3,4-dihydro-2,2-dimethyl-trans-4-(2-oxo-1-pyrrolidinyl) -2H-benzo-[b]pyran-3-ol.

A preferred class of pharmaceutically active ingredients is the class of anti-obesity agents, in particular those described in European Published Applications No. 0006735 such as N-[2-(4-carbomethoxyphenyl)-1-methylethyl]-2-hydroxy-2-phenylethanamine or a single steroisomer derived therefrom; or a pharmaceutically acceptable acid addition salt thereof, especially the hemi-fumarate salt.

A preferred class of pharmaceutically active ingredients is the class of anti-hyperglycaemic agents, in particular those described in European Patent No. 0023385 such as N-[2-(4-carbomethoxymethoxyphenyl)-1-methylethyl]-2-hydroxy-2-(3-chlorophenyl)ethanamine or a single stereoisomer derived therefrom; or a pharmaceutically acceptable acid addition salt thereof, especially the hydrobromide salt.

A preferred class of pharmaceutically active ingredients is the class of anti-emetic agents, in particular those described in European Published Patent Application No. 0200444, such as N-(endo-9-methyl-9-azabicyclo[3,3,1]non-3-yl)-1-methylindazole-3-carboxamide or a pharmaceutically acceptable salt thereof, especially the hydrochloride, or a solvate thereof.

A preferred class of pharmaceutically active ingredients is the class of gastric motility enhancing agents, in particular those described in European Published Patent Application No. 0094742 such as (±)4-amino-5-chloro-2-methoxy-N-(4'-[1'-azabicylco[3,3,1]-nonyl])-benzamide or a single isomer derived therefrom; or a pharmaceutically acceptable salt thereof, especially the hydrochloride salt, or an N-oxide thereof, or a hydrate thereof.

It has been found advantageous to dissolve these ingredients in a water miscible carrier, for example solketal or glycofurol, for absorption into a silica or silicate.

The freely flowable powder may be made by admixture of the liquid pharmaceutically active composition with the silica or silicate, with subsequent agitation to obtain homogeneous distribution of the composition in the silica or silicate.

The liquid pharmaceutically active composition may be made in a conventional manner, by admixture of a pharmaceutically active ingredient with a suitable liquid diluent or carrier.

In the case where the liquid diluent or carrier is a semi-solid material, formation of the freely flowable powder is conveniently carried out by heating together a mixture of silica or silicate and the semi-solid above the melting point of the semi-solid, and shaking the resulting mixture.

Tablets and capsules for administration may contain conventional excipients such as binding agents, acacia, gelatin, sorbitol, tragacanth, or polyvinylpyrrolidone: fillers, for example lactose, sugar, maize-starch, calcium phosphate, sorbitol or glycine; tabletting lubricants, for example magnesium stearate, talc, polyethylene glycol or silica; disintegrants, for example potato starch or cross-linked polyvinyl pyrrolidone; acceptable wetting agents such as sodium lauryl sulphate; and conventional flavouring or colouring agents.

Preferably the tablet or capsule formulation comprises greater than 30% w/w of the freely flowable silica or silicate.

Capsule formulations of the invention may be made in conventional manner, by filling the freely flowable powder into a capsule shell.

Tablet formulations of the invention may be made in conventional manner, by compacting the freely flowable powder, if necessary in the presence of a conventional excipient such as those described above.

The following Examples illustrate the invention. All experiments were conducted in a laboratory at ambient temperature and humidity.

EXAMPLE 1

Indomethacin capsules

A 25% w/v solution of Indomethacin was prepared in each of the following carriers.
(a) Glycofurol
(b) Dimethylisosorbide
(c) 25% Synperonic 8* in Dimethylisosorbide in each case, 5 g of Indomethacin was triturated with 20 ml of the solvent in a mortar using a pestle until the solute had dissolved completely.

5.5 ml of each solution was placed in a mortar and triturated with 3.7 g of silica (Sipernat 50) manually for 5 minutes affording a homogeneous solid. 1.15 g of cross-linked polyvinylpyrrolidone was added to the solid and the mixture triturated for a further 5 minutes. Sufficient quantity of this mix was filled by hand into a clear No. 2 hard gelatin capsule to give a drug content of 25 mg.

EXAMPLE 2

A mixture of 1.50 g of micronised Ketazolam and 10 ml of 25% Tween 80—Solketal, or dimethylisosorbide was triturated in a mortar using a pestle for 5 minutes to obtain an even dispersion. The mixture was allowed to stand at ambient conditions for four hours.

3.70 g of silica (Sipernat 50) was added to 5.5 ml of the above dispersion in a mortar and the mixture triturated for 5 minutes affording a homogeneous solid. To this solid was added 1.15 g of cross-linked polyvinylpyrrolidone and the solids were triturated for 5 minutes in the pestle and mortar.

221 mg of this mix was filled by hand into a clear No. 2 hard gelatin capsule, being equivalent to a Ketazolam content of 15 mg.

EXAMPLE 3

1.8 g of diazepam was added to 20 ml of Solketal in a mortar and the mixture was triturated with a pestle until the diazepam had completely dissolved.

5.5 ml of this solution was transferred to another mortar and to it was added 3.70 g of silica (Sipernat 50). The mixture was triturated by hand for 5 minutes affording a homogeneous solid, to which was added 1.15 g of cross-linked polyvinylpyrrolidone. Trituration of the solid mixture for five minutes with a pestle afforded the capsule filling mixture. 218 mg of mix, equivalent to 10 mg of diazepam, was filled by hand into clear No. 2 hard gelatin capsules.

EXAMPLE 4

19 ml of glycofurol and 1 ml of water were mixed in a pestle and mortar. To this liquid was added 0.05 g of digoxin and the mixture was triturated until the solid dissolved.

2 ml of this solution was added to 1.30 g of silica (Sipernat 50) in a mortar and the mixture triturated with a pestle for 5 minutes to yield a homogeneous solid. 0.35 g of cross-linked polyvinylpyrrolidone was added to the mortar and the mixture triturated for 5 minutes. 189 mg of mix, equivalent to 0.25 mg digoxin was filled by hand into clear No. 2 hard gelatin capsules.

EXAMPLE 5

Capsules of 6-cyano-3,4-dihydro-2,2-dimethyl-trans-4-(2-oxo-1-pyrrolidinyl)-2H-benzo-[b]pyran-3-ol.

The title compound can be formulated into capsules in a manner analogous to that described in Example 4.

EXAMPLE 6

Capsules of N-[2-(4-carbomethoxyphenyl)-1-methylethyl]-2-hydroxy-2-phenylethanamine, hemi-fumarate.

The title compound can be formulated into capsules in a manner analogous to that described in Example 4.

EXAMPLE 7

Capsules of N-[2-(4-carbomethoxymethoxyphenyl)-1-methylethyl]-2-hydroxy-2-(3-chlorophenyl)ethanamine, hydrobromide.

The title compound can be formulated into capsules in a manner analogous to that described in Example 4.

EXAMPLE 8

Capsules of
N-(Endo-9-methyl-9-azabicyclo[3,3,1]non-3-yl)-1-methylindazole-3-carboxamide, monohydrochloride.

The title compound can be formulated into capsules in a manner analogous to that described in Example 4.

EXAMPLE 9

Capsules of (±) 4-amino-5-chloro-2-methoxy-N-(4'-[1'-azabicyclo-[3,3,1]-nonyl])benzamide.

The title compound can be formulated into capsules in a manner analogous to that described in Example 4.

Experimental Results and Conclusions

Capsules of Example 1 were held in a copper wire twist and placed in 1500 ml of distilled water in a 2 litre round bottom flask, maintained at 37° C.±1° C. The water was stirred for 30 minutes with a USP (1980) paddle stirrer at 60 rpm, 5 ml samples being taken at regular intervals and assayed by UV spectroscopy at 317 nm wavelength. The latter wavelength is known to determine indomethacin in the presence of degradation products.

For comparison, commercially available Indocid 25 mg capsules, (Indocid is a trade mark), were subjected to the same treatment as above.

Indocid capsules were found to release their contents relatively slowly, and only 57% was released within 30 minutes. By contrast, release from the capsules of Example 1 was more rapid and more complete. After 30 mins, about 95% of the contents of the Indomethacin capsules of Example 1, using 25% Synperonic 8 in dimethylisosorbide as liquid carrier, were released.

I claim:

1. A pharmaceutical composition comprising a freely flowable powder, the powder comprising a porous, high absorption silica or silicate having a mean particle size of at least 10 μm in diameter and having absorbed therein at least 10% by volume of a liquid, pharmaceutically active composition, based on the weight of powder plus liquid, wherein said liquid pharmaceutically active composition comprises a pharmaceutically active ingredient selected from the group consisting of an anti-inflammatory agent, a tranquiliser, a cardiotonic agent, an antibacterial agent, an antidepressant, a corticosteroid, an anti-ulcer agent, an anti-allergy agent, an anti-obesity agent, an anti-hyperglycaemic agent, an anti-emetic agent and a gastric motility enhancing agent; and a liquid diluent or carrier.

2. The pharmaceutical composition as recited in claim 1 wherein the pharmaceutically active ingredient is the gastric motility enhancing agent (±) 4-amino-5-chloro-2-methoxy-N-(4'[1'-azabicyclo-[3,3,1]-noyl])-benzamide.

3. The pharmaceutical composition as recited in claim 1 wherein the pharmaceutically active ingredient is the anti-emetic agent N-(Endo-9-methyl-9-azabicyclo[3,3,1]non-3-yl-1-methyl-indazole-3-carboxamide.

4. The pharmaceutical composition as recited in claim 1 wherein the pharmaceutically active ingredient is the anti-hyperglycaemic agent N-[2-(4-carbomethoxymethoxyphenyl)-1-methylethyl]-2-hydroxy-2-(3-chlorophenyl)ethanamine.

5. The pharmaceutical composition as recited in claim 1 wherein the pharmaceutically active ingredient is the anti-obesity agent N-[2-(4-carboxymethoxyphenl)-1-methyl-ethyl]-2-hydroxy-2-phenylethanamine or a pharmaceutically acceptable acid addition salt thereof.

6. A pharmaceutical composition comprising a freely flowable powder, the powder comprising a porous, high absorption silica or silicate having a mean particle size of at least 10 μm in diameter and having absorbed therein at least 10% by volume of a liquid, pharmaceutically active composition, based on the weight or powder plus liquid, wherein said liquid pharmaceutically active composition comprises a pharmaceutically active ingredient selected from the group consisting of (±) 4-amino-5-chloro-2-methoxy-N-(4'[1'-azabicyclo-[3,3,1]-non-1])-benzamide, N-[2-(4-carbomethoxymethoxyphenyl)-1-methylethyl[-2-hydroxy-2-(3-chlorophenyl)ethanamine, N-(Endo-9-methyl-9-azabicyclo[3,3,1]non-3-yl)-1-methyl-indazole-3-carboxamide and N--methylindazole-3-carboxamide and N-[2-(4-carboxymethozyphenyl)-1-methyl-ethyl]-2-hydroxy-2-phenylethanamine or a pharmaceutically acceptable acid addition salt thereof; and a liquid diluent or carrier.

7. A pharmaceutical composition comprising a freely flowable powder, the powder comprising a porous, high absorption silica or silicate having a mean particle size of at least 10 μm in diameter and having absorbed therein at least 10% by volume of a liquid, pharmaceutically active composition, based on the weight of powder plus liquid, wherein said liquid pharmaceutically active composition comprises a pharmaceutically active ingredient selected from the group consisting of anti-obesity agent, an anti-hyperglycaemic agent, an anti-emetic agent and gastric motility enhancing agent; and a liquid diluent or carrier.

* * * * *